United States Patent [19]

Duc

[11] Patent Number: 4,966,989
[45] Date of Patent: Oct. 30, 1990

[54] PROCESS FOR THE PRODUCTION OF 4-CHLORO-3-ALKOXY-BUT-2E-ENOIC ACID ALKYL ESTERS

[75] Inventor: Laurent Duc, Sion, Switzerland

[73] Assignee: Lonza Ltd., Gampel, Switzerland

[21] Appl. No.: 362,965

[22] Filed: Jun. 8, 1989

[30] Foreign Application Priority Data

Jun. 14, 1988 [CH] Switzerland .................. 2288/88

[51] Int. Cl.$^5$ .............................................. C07C 69/73
[52] U.S. Cl. ..................................... 560/183; 560/184
[58] Field of Search ................................ 560/183, 184

[56] References Cited

U.S. PATENT DOCUMENTS

| | | | |
|---|---|---|---|
| 2,571,212 | 10/1951 | Croxall et al. | 560/183 |
| 2,864,852 | 12/1958 | Jones | 560/183 |
| 4,812,593 | 3/1989 | Hoelderich et al. | 560/183 |

FOREIGN PATENT DOCUMENTS 0216324 4/1987 European Pat. Off. .

*Primary Examiner*—Bruce Gray
*Attorney, Agent, or Firm*—Fisher, Christen & Sabol

[57] ABSTRACT

A process for the production of 4-chloro-3-alkoxy-but-2E-enoic acid alkyl esters starting from 4-chloroacetoacetic acid chloride by reaction with a dialkyl sulfite. The produced intermediate products are used as structural elements for, i.a., pharmaceutical agents.

12 Claims, No Drawings

PROCESS FOR THE PRODUCTION OF 4-CHLORO-3-ALKOXY-BUT-2E-ENOIC ACID ALKYL ESTERS

BROAD DESCRIPTION OF THE INVENTION

The object of the invention is to provide a process for the production of 4-chloro-3-alkoxy-but-2E-enoic acid alkyl esters. Other objects and advantages of the invention are set out herein or are obvious herefrom to one skilled in the art.

4-chloro-3-alkoxy-but-2E-enoic acid alkyl esters are versatile structural elements for numerous syntheses of active ingredients, for i.a., pharmaceutical agents, agrochemicals, etc. For example, these intermediate products are used in the production of 4-hydroxy-2-oxo-pyrrolidin-1-yl acetamide, a cerebrally active pharmaceutical agent (European Published Patent Application No. 0216324). European Published Patent Application No. 0216324 discloses that the 4-chloro-3-alkoxy-but-2E-enoic acid alkyl esters can be produced by reaction of 4-chloroacetoacetic acid alkyl ester with an orthoformic acid trialkyl ester in the presence of sulfuric acid to ketal ester and heating in a vacuum. Good yields of 90 to 93 percent are indeed possible according to these known methods but, on the one hand, the insufficient purity of the resultant product is disadvantageous and, on the other hand, the high cost of the orthoformic acid trialkyl ester is a burden on the production costs of a multiple stage active ingredient synthesis. Moreover, considered from the safety viewpoint, the formation of the extremely toxic dimethyl sulfate in the reaction of orthoformic acid trialkyl ester with sulfuric acid is not safe. Therefore, another object of the invention is to provide a process which does not exhibit said drawbacks and which produces 4-chloro-3-alkoxy-but-2E-enoic acid alkyl esters on an industrial scale in a cost-favorable and safe manner.

The objects of the invention are achieved according to the invention process. The invention process involves the production of 4-chloro-3-alkoxy-but-2E-enoic acid alkyl esters of the formula:

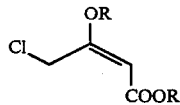

wherein R is an alkyl having 1 to 4 C atoms. The -chloroacetoacetic acid chloride is reacted with a dialkyl sulfite of the formula:

(RO)$_2$S=O and the corresponding alcohol ROH to provide a ketal ester of the formula:

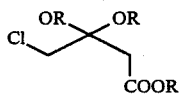

The ketal ester is reacted without isolation by warming under reduced pressure in the presence of an acid to provide the end product.

DETAILED DESCRIPTION OF THE INVENTION

The initial reactant of the process is 4-chloroacetoacetic acid chloride, which is produced on a large scale from diketene and chlorine, preferably dissolved in methylene chloride.

The reaction of the 4-chloroacetoacetic acid chloride to the ketal ester of the formula:

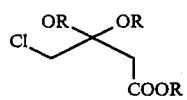

wherein R is an alkyl having 1 to 4 C atoms, takes place then with dialkyl sulfite, produced in situ, of the formula:

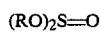

(RO)$_2$S=O and the corresponding alcohol ROH. Dialkyl sulfite produced in situ means that, by the addition of thionyl chloride and the corresponding alcohol to the reaction mixture, the necessary amount of dialkyl sulfite is generated and is immediately available for ketal formation. An additional amount of the corresponding alcohol ROH is necessary to convert the acid chloride into the ester. Therefore, an excess of alcohol ROH is suitably used. The total amount of alcohol suitably varies between 5 and 20 mol per mol of 4-chloroacetoacetic acid chloride. Especially lower aliphatic alcohols, such as, methanol, ethanol, propanol and butanol, are used as suitable alcohols ROH in regard to the substituents R in the end product and its further use.

Since the 4-chloroacetoacetic acid chloride is taken directly from the production process (from diketene and chlorine), it is present in the form of a solution, suitably in an inert solvent such as methylene chloride.

Another advantage of the process according to the invention is that the solution of 4-chloroacetoacetic acid chloride can be used directly for reaction to the ketal ester. The reaction to the ketal ester is suitably performed at a temperature between −10° and 120° C., preferably at room temperature. From experience, a reaction time of 2 to 5 hours is normally required. The ketal ester can indeed be isolated, but advantageously it is further reacted directly to the desired end product.

For this purpose, the reaction mixture, suitably after previous removal of the solvent, is mixed with an acid and is converted to the end product by warming at reduced pressure. Sulfuric acids or a sulfonic acid, such as, methanesulfonic acid or p-toluenesulfonic acid, in catalytic amounts of 0.4 to 1 mol percent are suitably used as acids. The temperatures for the conversion of the ketal ester to the end product are suitably between 70° and 150° C., preferably between 100° and 130° C. In the conversion a reduced pressure between 50 and 500 mbars, advantageously between 75 and 100 mbars, is maintained. The resultant 4-chloro-3-alkoxy-but-2E-enoic acid alkyl ester after this treatment can be isolated and optionally purified in the usual way.

According to the process of the invention, yields of about 90 percent and purities of the products of greater than 99 percent can be attained. As used herein, all parts, percentages, ratios and proportions are on a weight basis unless otherwise stated herein or otherwise obvious herefrom to one skilled in the art.

EXAMPLE 1

4-chloro-3-methoxy-but-2E-enoic acid methyl ester 206.6 g (0.47 mol) of a 35 percent mixture of 4-chloroacetoacetyl chloride in methylene chloride was cooled to −10° C. Under nitrogen, 102.4 g (3.2 mol) of methanol was added in 30 minutes and then 83.3 g (0.7 mol) of thionyl chloride was added in 30 minutes (formation of dimethyl sulfite). The temperature was raised to room temperature and the solution was stirred for 3 hours at 20° to 25° C. The excess methanol and methylene chloride were then distilled off at reduced pressure. The residue (raw 4-chloro-3,3-dimethoxybutanoic acid methyl ester) was mixed with 0.21 g of methanesulfonic acid and warmed to 125° to 130° C. at a pressure of 100 mbars. Thus, the formed methanol and the excess dimethyl sulfite was distilled off. The residue (raw 4-chloro-3-methoxy-but-2E-enoic acid methyl ester) was taken up in 110.2 g (120 ml) of toluene and the organic phase was washed with 69.8 g of aqueous 16 percent HCl for 30 minutes, with 32.1 g of an aqueous 10 percent sodium chloride solution for 10 minutes, with 134 g of aqueous 10 percent NaOH for 75 minutes and finally with 32.1 g of an aqueous 10 percent sodium chloride solution for 10 minutes. The toluene was then evaporated off and the residue was distilled at a pressure of 20 mbars and a temperature of 95° to 97° C. 4-chloro-3-methoxybut-2E-enoic acid methyl ester was obtained in a yield of 61.7 g (80 percent) in a purity of 99.5 percent (GC).

EXAMPLE 2

4-chloro-3-ethoxy-but-2E-enoic acid ethyl ester 206.6 g (0.47 mol) of a 35 percent mixture of 4-chloroacetoacetyl chloride in methylene chloride was cooled to −10° C. Under nitrogen, 147.2 g (3.2 mol) of ethanol was added in 30 minutes, and then 83.3 g (0.7 mol) of thionyl chloride was added in 30 minutes (formation of diethyl sulfite). The temperature was raised to 55° to 60° C. in an hour, and then it was stirred for 1 hour more at 55° to 60° C. Then the excess ethanol and methylene chloride was distilled off at reduced pressure. The residue (raw 4-chloro-3,3-diethoxybutanoic acid ester) was mixed with 0.27 g of methanesulfonic acid and warmed at a pressure of 75 mbars to 125° to 130° C. Thus, the formed ethanol and excess diethyl sulfite were distilled off. The residue (raw 4-chloro-3-ethoxy-but-2E-enoic acid ethyl ester) was taken up in 110.2 g (120 ml) of toluene and the organic phase was washed with 69.8 g of aqueous 16 percent HCl for 30 minutes, with 32.1 g of an aqueous 10 percent sodium chloride solution for 10 minutes, with 134 g of aqueous 10 percent NaOH for 75 minutes and finally with 32.1 g of aqueous 10 percent sodium chloride solution for 10 minutes. The toluene was then evaporated off and the residue was distilled at a pressure of 2 mbars and a temperature of 78° to 80° C. 4-chloro-3-ethoxy-but-2E-enoic acid ethyl ester was obtained in a yield of 80.6 g (88.5 percent) in a purity of 99.8 percent (GC).

What is claimed is:

1. Process for the production of 4-chloro-3-alkoxy-but-2E-enoic acid alkyl esters of the formula:

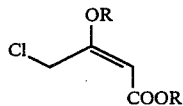

wherein R is an alkyl with 1 to 4 C atoms, characterized in that 4-chloroacetoacetic acid chloride is reacted with a dialkyl sulfite of the formula:

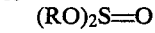

$(RO)_2S=O$ wherein R is the same as defined above, and the corresponding alcohol ROH, wherein R is the same as defined above, to the ketal ester of the formula:

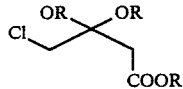

wherein R is the same as defined above, and said ketal ester is reacted without isolation by warming under reduced pressure in the presence of an acid to the end product.

2. Process according to claim 1 wherein the dialkyl sulfite is produced in situ by reaction of thionyl chloride with the corresponding alcohol ROH.

3. Process according to claim 2 wherein the alcohol for the in situ dialkyl sulfite formation and the alcohol for the ester formation are added at the same time in an amount from 5 to 20 mol, relative to 1 mol of 4-chloroacetoacetic acid chloride.

4. Process according to claim 3 wherein the reaction to the ketal ester takes place at a temperature from −10° to 120° C.

5. Process according to claim 4 wherein the reaction to the ketal ester takes place in the presence of an inert solvent.

6. Process according to claim 5 wherein the dialkyl sulfite produced in situ is present in a molar ratio of 2 to 1 and 1.4 to 1 to the 4-chloroacetoacetic acid chloride.

7. Process according to claim 1 wherein the conversion of the ketal ester to the end product takes place at a temperature between 70° and 150° C. and at a pressure between 50 and 500 mbars.

8. Process according to claim 7 wherein the conversion of the ketal ester to the end product takes place in the presence of a catalytic amount of 0.4 to 1 mol percent of sulfuric acid or a sulfonic acid.

9. Process according to claim 1 wherein the reaction to the ketal ester takes place at temperatures from −10° to 120° C.

10. Process according to claim 1 wherein the reaction to the ketal ester takes place in the presence of an inert solvent.

11. Process according to claim 1 wherein the conversion of the ketal ester to the end product takes place in the presence of a catalytic amount of 0.4 to 1 mol percent of sulfuric acid or a sulfonic acid.

12. Process according to claim 1 wherein the dialkyl sulfite is produced in situ by reaction of thionyl chloride with the corresponding alcohol ROH, the dialkyl sulfite produced in situ being present in a molar ratio of 2 to 1 and 1.4 to 1 to the 4-chloroacetoacetic acid chloride.

* * * * *